(12) United States Patent
Maloisel et al.

(10) Patent No.: US 10,864,512 B2
(45) Date of Patent: Dec. 15, 2020

(54) CHROMATOGRAPHY MATRIX

(71) Applicant: GE HEALTHCARE BIOPROCESS R&D AB, Uppsala (SE)

(72) Inventors: Jean-Luc Maloisel, Uppsala (SE); Tobias Söderman, Uppsala (SE); Ola Lind, Uppsala (SE); Ida Eklind, Uppsala (SE)

(73) Assignee: Cytiva BioProcess R&D AB, Uppsala (SE)

( * ) Notice: Subject to any disclaimer, the term of this patent is extended or adjusted under 35 U.S.C. 154(b) by 57 days.

(21) Appl. No.: 16/090,609

(22) PCT Filed: Mar. 30, 2017

(86) PCT No.: PCT/EP2017/057482
§ 371 (c)(1),
(2) Date: Oct. 2, 2018

(87) PCT Pub. No.: WO2017/174422
PCT Pub. Date: Oct. 12, 2017

(65) Prior Publication Data
US 2019/0111419 A1 Apr. 18, 2019

(30) Foreign Application Priority Data

Apr. 6, 2016 (GB) .................................. 1605870.3

(51) Int. Cl.
*B01D 15/32* (2006.01)
*B01D 15/36* (2006.01)
(Continued)

(52) U.S. Cl.
CPC ............ *B01J 47/02* (2013.01); *B01D 15/327* (2013.01); *B01D 15/362* (2013.01);
(Continued)

(58) Field of Classification Search
CPC ... B01J 47/02; B01J 39/19; B01J 39/07; B01J 39/26; B01J 41/07; B01J 41/13;
(Continued)

(56) References Cited

U.S. PATENT DOCUMENTS

| 5,135,650 A | 8/1992 | Hjerten et al. |
| 2005/0222279 A1 | 10/2005 | Larsson et al. |

(Continued)

FOREIGN PATENT DOCUMENTS

WO WO-2013162449 A1 * 10/2013 ............ B01J 20/286

OTHER PUBLICATIONS

PCT International Search Report and Written Opinion for PCT Application No. PCT/EP2017/057482 dated May 19, 2017 (13 pages).

(Continued)

*Primary Examiner* — Benjamin L Lebron
(74) *Attorney, Agent, or Firm* — Eversheds Sutherland (US) LLP (57) ABSTRACT

The invention discloses a separation matrix for purification of biomacromolecules, comprising a plurality of particles (1) having a core region (2) and a shell region (3), wherein: a) said shell region is accessible to a target biomacromolecule; b) said core region is less accessible to the target biomacromolecule than the shell region; and c) the core region comprises a grafted polymer comprising residues of at least one polymerizable monomer.

33 Claims, 8 Drawing Sheets

(51) Int. Cl.
*B01D 15/38* (2006.01)
*B01J 20/26* (2006.01)
*B01J 20/286* (2006.01)
*B01J 20/289* (2006.01)
*B01J 20/32* (2006.01)
*B01J 39/07* (2017.01)
*B01J 39/26* (2006.01)
*B01J 41/07* (2017.01)
*B01J 41/13* (2017.01)
*B01J 41/20* (2006.01)
*B01J 47/02* (2017.01)
*C07K 1/18* (2006.01)
*C07K 16/00* (2006.01)
*B01J 39/19* (2017.01)

(52) U.S. Cl.
CPC ....... *B01D 15/363* (2013.01); *B01D 15/3809* (2013.01); *B01D 15/3847* (2013.01); *B01J 20/267* (2013.01); *B01J 20/286* (2013.01); *B01J 20/289* (2013.01); *B01J 20/3208* (2013.01); *B01J 20/3217* (2013.01); *B01J 20/3219* (2013.01); *B01J 20/3278* (2013.01); *B01J 20/3285* (2013.01); *B01J 20/3293* (2013.01); *B01J 39/07* (2017.01); *B01J 39/19* (2017.01); *B01J 39/26* (2013.01); *B01J 41/07* (2017.01); *B01J 41/13* (2017.01); *B01J 41/20* (2013.01); *C07K 1/18* (2013.01); *B01D 15/361* (2013.01); *B01D 15/3804* (2013.01); *B01J 2220/54* (2013.01); *C07K 16/00* (2013.01)

(58) Field of Classification Search
CPC ........ B01J 41/20; B01J 20/267; B01J 20/286; B01J 20/289; B01J 20/3208; B01J 20/3217; B01J 20/3219; B01J 20/3279; B01J 20/3285; B01J 20/3293; B01J 2220/54; B01J 20/3278; B01D 15/327; B01D 15/361; B01D 15/362; B01D 15/363; B01D 15/3809; B01D 15/3804; B01D 15/3847; C07K 1/18; C07K 16/00

See application file for complete search history.

(56) References Cited

U.S. PATENT DOCUMENTS

| | | |
|---|---|---|
| 2007/0196858 A1 | 8/2007 | Glad et al. |
| 2007/0212540 A1* | 9/2007 | Cheng .................... B01J 20/262 428/402 |
| 2007/0244307 A1* | 10/2007 | Engstrand .......... B01D 15/3809 530/417 |
| 2010/0036055 A1 | 2/2010 | Hayashi et al. |
| 2010/0075131 A1* | 3/2010 | Etzel .................. B01D 39/1676 428/315.5 |
| 2011/0003941 A1 | 1/2011 | Andersson et al. |
| 2012/0029154 A1 | 2/2012 | Deetz et al. |
| 2012/0143081 A1 | 6/2012 | Lyu |
| 2012/0309618 A1 | 12/2012 | Bergstrom et al. |
| 2013/0225701 A1* | 8/2013 | Soice ................. B01J 20/28085 521/31 |
| 2015/0133618 A1 | 5/2015 | Hanssen et al. |

OTHER PUBLICATIONS

GB Search Report for GB Application No. 1605870.3 dated Jan. 5, 2017 (3 pages).

Bhattacharya et al., "Grafting: A Versatile Means to Modify Polymers Techniques, Factors and Applications," Prog. Polym. Sci., 2004, 29:767-814.

Gel Filtration Principoles and Methods, 5th Edition, Pharmacia LKB, 1991, pp. 8-11 (ISBN 91-97-0490-2-6).

* cited by examiner

CHROMATOGRAPHY MATRIX

CROSS REFERENCE TO RELATED APPLCATIONS

This application claims the priority benefit of PCT/EP2017/057482 filed on Mar. 30, 2017 which claims priority benefit of Great Britain Application No. 1605870.3 filed Apr. 6, 2016. The entire contents of which are hereby incorporated by reference herein.

TECHNICAL FIELD OF THE INVENTION

The present invention relates to the field of chromatography, and more specifically to chromatography matrices with a dense core region and a porous shell region.

BACKGROUND OF THE INVENTION

In liquid chromatography separations the resolution increases with decreasing particle size of the porous packing material. This is due to the shorter diffusion distances inside the particles, which leads to a higher column efficiency, often measured as the plate number of the column. A drawback is however that the smaller particle size leads to higher column back pressures, which is a strong cost driver, particularly for preparative chromatography where miniaturization of columns is not a possible route.

One way to decouple the resolution from the particle size has been to use pellicular media, where a non-porous core is coated by a thin layer of porous stationary phase material. Such media have however not been used to a great extent in preparative separations of biomacromolecules, due to difficulties of manufacturing pellicular media with properties equal to those of regularly used biomacromolecule separation media, where low degrees of non-specific adsorption of proteins etc, high accessibility to biomacromolecules and high binding capacities are important parameters.

There is thus a need in this field for new developments allowing biomacromolecule separations with improved resolution while maintaining advantages of non-pellicular biomacromolecule separation media such as low non-specific adsorption, reasonable capacities and high selectivities for important target biomacromolecules.

SUMMARY OF THE INVENTION

One aspect of the invention is to provide a high resolution separation matrix for purification of biomacromolecules such as proteins. This is achieved with a matrix comprising a plurality of particles with a core region comprising a grafted polymer and a shell region, wherein the shell region is accessible to a target biomacromolecule and the core region is less accessible to the target biomacromolecule than the shell region.

One advantage is that a high resolution can be provided without having to resort to small particles, which cause issues with high back pressures and low flow rates.

A second aspect of the invention is to provide a method of manufacturing a high resolution separation matrix. This is achieved with a method comprising the steps of:
a) providing a plurality of particles comprising a porous support material;
b) introducing grafting sites on the porous support material;
c) inactivating the grafting sites in a shell region;
d) incubating the particles in a composition comprising a polymerizable monomer; and
e) initiating polymerization.

This method produces a matrix as disclosed above and having the same advantages.

A third aspect of the invention is to provide a method of separating a target biomolecule from a sample by conveying the sample through a column packed with the separation matrix as disclosed above, optionally conveying a wash liquid through the column and conveying an eluent through the column to recover the target biomacromolecule in an eluate.

A fourth aspect of the invention is to provide a use of the separation method disclosed above for improving resolution between a target biomacromolecule and at least one contaminant.

Further suitable embodiments of the invention are described in the dependent claims.

Definitions

The terms "antibody" and "immunoglobulin" are used interchangeably herein, and are understood to include also fragments of antibodies, fusion proteins comprising antibodies or antibody fragments and conjugates comprising antibodies or antibody fragments.

The term "affinity chromatography matrix" herein means a separation matrix having ligands (here described as "affinity ligands" or "ligands comprising affinity groups") capable of binding a target species with an equilibrium dissociation constant $K_D$ less than about $10^{-5}$ M, such as between $10^{-14}$ and $10^{-6}$ M. $K_D$ is here defined as $K_D=[L]*[T]/[LT]$, where [L] is the concentration of free ligand, [T] is the concentration of free target species and [LT] is the concentration of ligand-target species complex. Most such ligands/groups are proteins and can e.g. include bacterial immunoglobulin-binding proteins and their variants, antibodies, streptavidin, lectins etc. The target species can e.g. be a protein such as an immunoglobulin.

DETAILED DESCRIPTION OF EMBODIMENTS

Figure 1:
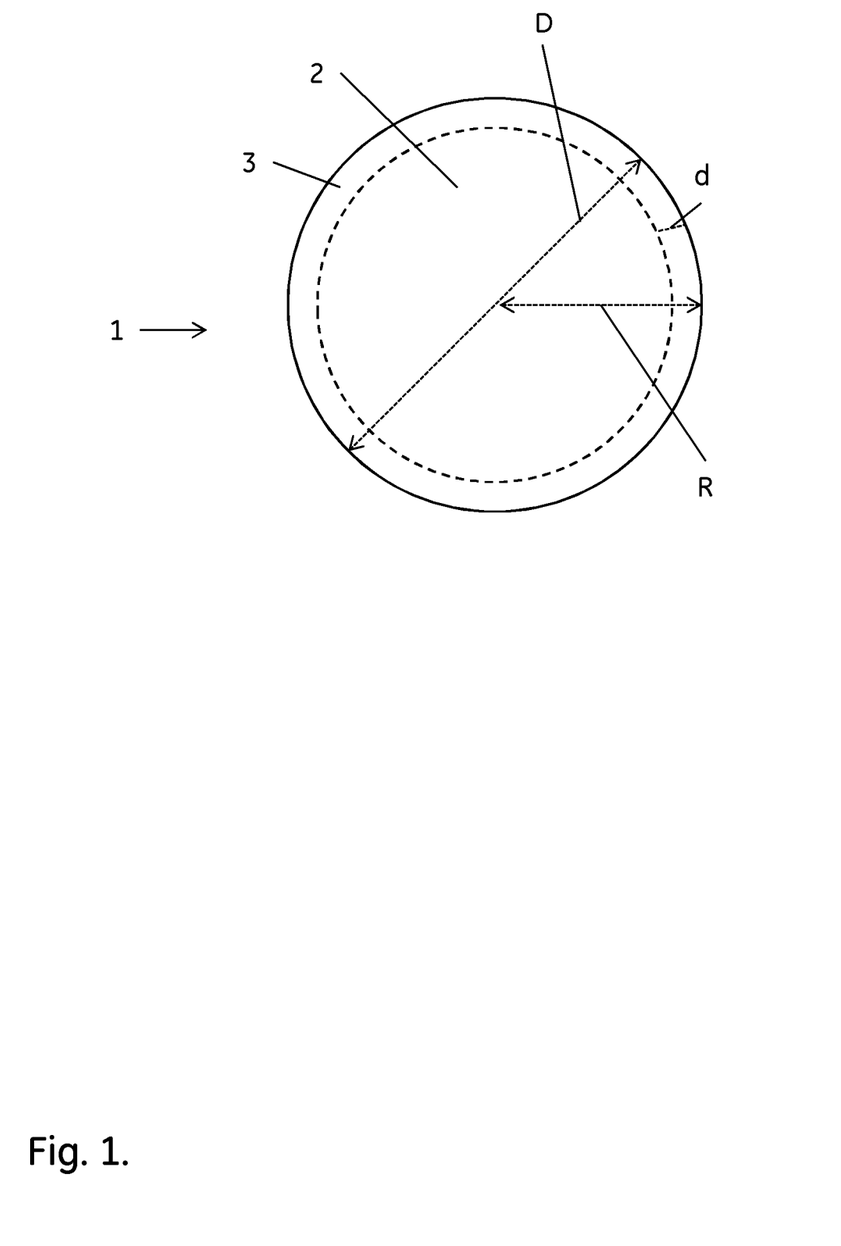
FIG. 1 shows a schematic drawing of the matrix of the invention.

In one aspect, the present invention discloses a separation matrix for purification of biomacromolecules. The separation matrix comprises a plurality of particles 1 having a central core region 2 and a peripheral shell region 3. The core region comprises a grafted polymer (P) comprising residues of at least one polymerizable monomer, e.g. a vinyl monomer, and while the shell region is accessible to a target biomacromolecule, the core region is less accessible to the target biomacromolecule than the shell region. The diffusion rate for the target biomacromolecule in the core region may e.g. be less than 10% of the diffusion rate for the target biomacromolecule in the shell region and suitably, the core region may be substantially inaccessible to the target biomacromolecule. The accessibility can be measured by inverse size exclusion chromatography at e.g. 20-50 cm/h flow velocity, as outlined in Gel Filtration Principles and Methods 5$^{th}$ edition, Pharmacia LKB 1991 (ISBN 91-97-0490-2-6), pp 8-11 and in the Examples. Alternatively, confocal microscopy can be used to evaluate the accessibility. In this case a fluorescence labeled target biomacromolecule may be used as a probe and the fluorescence intensity of the different regions can be measured in the confocal microscope and taken as a measure of the accessibility. The fluorescence intensity in the core region may e.g. be less than 90%, such as less than 70%, less than 50% or less than 10% of the fluorescence intensity in the shell region. The target biomacromolecule may be a protein, e.g. with a molecular weight of >5, >20 or over 50 kDa, and in particular an immunoglobulin such as IgG, with a molecular weight of about 150 kDa. The core region can suitably contain at least 50 mg/ml of the grafted polymer, such as at least 70 mg/ml or 50-300, such as 50-200 or 70-150 mg/ml, to significantly reduce the accessibility for common biomacromolecules. Determination of the polymer amount can either be done during manufacturing as illustrated in the examples or on the final product. In the latter case, e.g. spectroscopic methods or elemental analysis may be used. In comparison with pellicular matrices having a core which is subsequently coated with a porous material, the matrix of the invention has a more well-controlled structure and is easier to manufacture, with controlled variation in shell thickness and polymer content.

In certain embodiments, the shell region has an average thickness d of 1-15 micrometers. Alternatively, or additionally, the average thickness may be 0.5 to 6% of the volume-weighted median diameter or sphere-equivalent diameter of the particles. The particles may be substantially spherical, but they may also deviate from spherical shape, e.g. having an average sphericity of at least 0.9, such as at least 0.95 or at least 0.98 (a sphere has a sphericity of 1). The particles may e.g. have a volume-weighted median diameter of 10-400 micrometers, such as 20-400, 30-100 micrometers or 50-100 micrometers.

In certain embodiments, the shell region and the core region both comprise a porous support material. The porous support material may e.g. comprise a polysaccharide, which can be cross-linked. Examples of suitable polysaccharides include agarose and agar, which provide open pore structures with high accessibility to proteins and which are amenable to pore-filling by grafting of vinyl polymers.

In some embodiments, the core region has a molecular weight cutoff for globular proteins of 1 to 500 kDa, such as 60-500, 80-200 or 80-140 kDa.

The polymer (Pol) may e.g. be grafted to the support material (Sup), i.e. by polymerization of monomers leading to covalent attachment of polymer chains to the support material. The bonds or linkers between the polymer chains and the support material may e.g. be of structure I, II, III, IV or V.

| Sup-O—CH$_2$—CH$_2$—CH$_2$-Pol | (I) |
| Sup-O—CH$_2$—CH(CH$_3$)-Pol | (II) |
| Sup-O—CH$_2$—CHOH—CH$_2$—O—CH$_2$—CH$_2$—CH$_2$-Pol | (III) |
| Sup-O—CH$_2$—CHOH—CH$_2$—O—CH$_2$—CH(CH$_3$)-Pol | (IV) |
| Sup-O-Pol | (V) |

Structures I and II may e.g. be formed by grafting via allyl groups introduced through reaction of support hydroxyls with an allyl halide and structures III and IV may be formed by grafting via allyl groups introduced through reaction of support hydroxyls with allyl glycidyl ether. Structure V may e.g. be formed by grafting from immobilized peroxides or hydroperoxides on the support. The attachment of polymer by graft polymerization of monomers has the advantage that high concentrations of grafted polymer may be achieved, since the small monomer molecules can still diffuse into the core while the pores are being gradually blocked through filling with grafted polymer. Attachment of ready-made polymer is generally less successful, as the large polymer molecules will be at least partially excluded from the core as soon as the pore filling starts. The polymer (P) may be a vinyl polymer and may e.g comprise vinyl amide monomer residues, such as residues selected from the group consisting of N-vinyl pyrrolidone, N-vinyl caprolactam, N-vinyl formamide and N-vinyl acetamide. It can e.g. comprise N-vinyl pyrrolidone residues, which are stable towards cleaning with 1 M NaOH and are hydrophilic.

The shell region may be devoid of biomacromolecule (e.g. protein)-binding functionalities, in which case the particles may be used for size exclusion chromatography separations (also called gel filtration). However, in certain embodiments the shell region comprises ligands capable of binding the target biomacromolecule. This enables the use of the particles for a range of chromatographic techniques. For ion exchange chromatography, the ligands can comprise positively (anion exchange) or negatively (cation exchange) charged groups. Examples of positively charged groups include quaternary ammonium groups and amines, while examples of negatively charged groups include e.g. sulfonates, sulfates, carboxylates and phosphonates. The ligands may also, or alternatively, comprise hydrophobic groups such as alkyl-alkylene-, aryl- or alkylaryl groups. These can be useful for hydrophobic interaction chromatography. Matrices with ligands comprising both charged and hydrophobic groups can be useful for multimodal chromatography separations and examples of such multimodal ligands include N-benzyl-N-methyl ethanolamine, N-benzoyl homocysteine, 4-mercaptoethyl pyridine, p-aminobenzamidoacetic acid, tryptophan, phenylalanine etc. The ligands can further comprise affinity groups, such that the matrix becomes useful for affinity chromatography. Examples of such affinity groups include Protein A and Protein A variants, Protein L, Protein G, antibodies, lectins, biotin, avidin, aptamers etc. The amount of ligands in the shell region can vary depending on the application and the type of ligands but, as a rule of thumb, the shell region may e.g. comprise 10-20 000 micromol ligand/ml shell region, such as 10-10 000 micromol/ml or 10-2000 micromol/ml. The shell region ligand content can be determined by densitometry in confocal microscopy, using a fluorescent dye that binds to the ligands and calibration curves from particles with known ligand concentration. It can also be determined from titrations of the entire particles, giving the ligand content per volume matrix and dividing by the shell volume fraction of the matrix.

Figure 2:
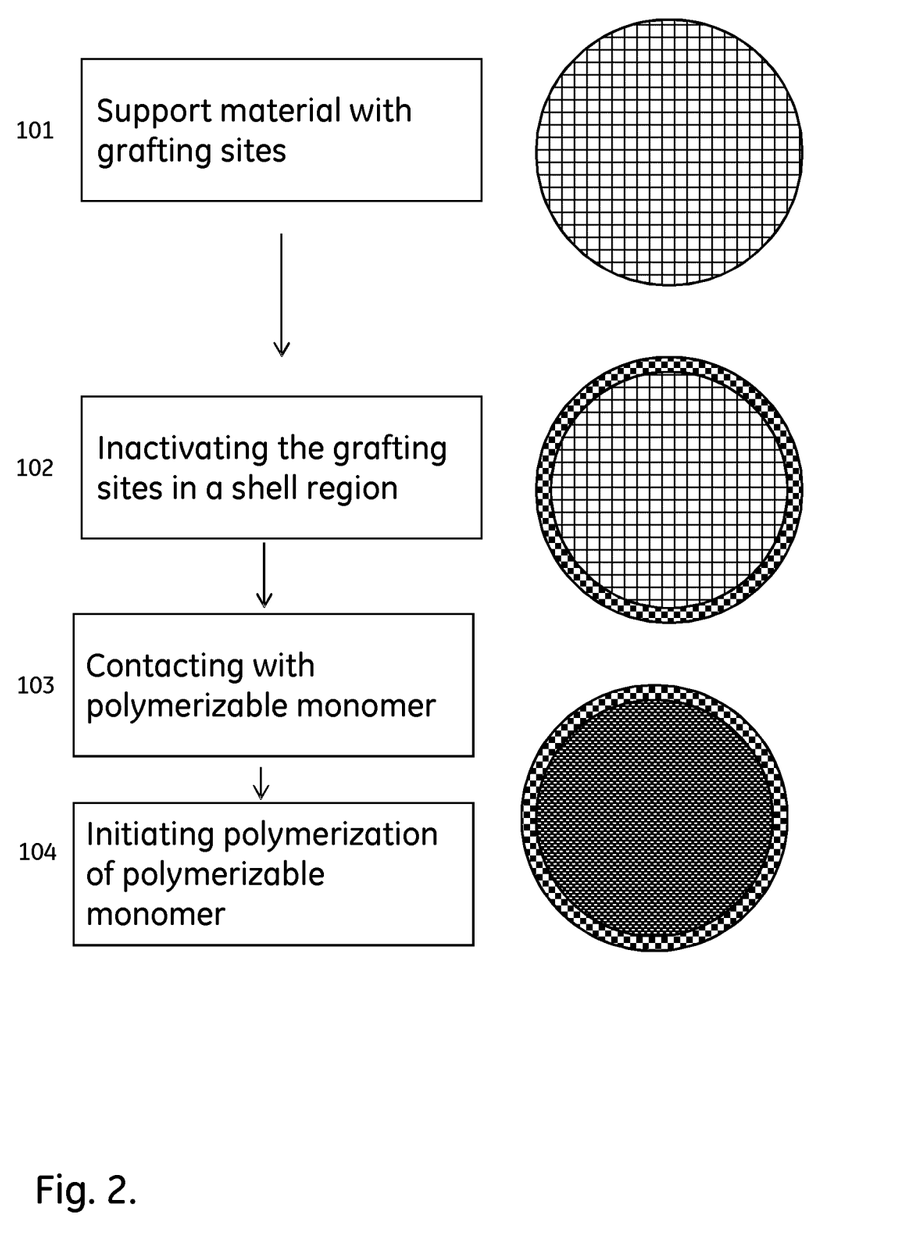
FIG. 2 shows a scheme for the manufacturing of the matrix of the invention.

In a second aspect the current invention discloses a method of manufacturing a separation matrix as disclosed above. The method comprises the steps of:

a) providing a plurality of particles comprising a porous support material with grafting sites 101.

The support material may comprise intrinsic grafting sites, e.g. polydivinylbenzene beads with residual vinyl groups or polysaccharide beads with hydroxyl groups amenable to anion polymerization of epoxides etc. or with alpha carbons amenable to radical grafting by e.g. cerium ion initiation. Alternatively, the grafting sites may be introduced on the porous support material in a step a'), before step a). This can involve e.g. derivatization of hydroxyl groups in polysaccharide beads with allyl groups or other copolymerizable groups or it can involve the immobilization of radical initiator functionalities, e.g. peroxides or hydroperoxides. Different methods of introducing grafting sites are discussed in U.S.20120029154 and in A Bhattacharya et al, Prog. Polym. Sci. 767-814 (2004), which are hereby incorporated by reference in their entireties. As discussed above, the porous support material may be cross-linked or non-cross-linked polysaccharide particles/beads, such as agar or agarose particles/beads, but it can also be other types of materials, such as porous synthetic polymer particles/beads (e.g. made from divinylbenzene or styrene/divinylbenzene polymers or various acrylate, methacrylate or vinyl ether polymers), silica or glass particles/beads etc.

b) inactivating the grafting sites in a shell region 102.

The inactivation can suitably be performed by the addition of a controlled amount (a deficit) of a reagent that inactivates the grafting sites, and since the reagent is added from the outside of the particles, the reagent will primarily react with grafting sites in a peripheral shell region. Suitably, the reaction rate between the reagent and the grafting sites is higher than the diffusion rate of the reagent in the particles, so that the reagent is consumed before any appreciable diffusion into the core takes place. The thickness of the inactivated shell layer can then be controlled by the amount of reagent added. For calculation of the shell thickness, it can be assumed that all grafting sites in the shell have been consumed by the inactivation reagent and that all grafting sites in the core remain. The ratio of the grafting site content after inactivation ($g_a$) and the grafting site content before inactivation ($g_b$) will then be equal to the core/(core+shell) volume ratio. Thus, the shell thickness d will be $d=R(1-(g_a/g_b)^{1/3})$, where R is the bead radius. The nature of the inactivating reagent varies depending on the structure of the grafting sites. For unsaturated grafting sites (allyls, vinyls etc.), a halogen such as bromine can be a suitable choice. Halogens react rapidly with double bonds and make them non-reactive in polymerizations. Reaction with halogens in aqueous solution, e.g. using bromine water, also has the advantage that halohydrins are formed, which can be used for derivatization of the shell region with ligands (e.g. nucleophilic ligand precursor reagents like amines, thiols or sulfite ions). However, unsaturated grafting sites can also be inactivated in other ways, e.g. by addition reactions with thiols. Hydroxyls as grafting sites can be inactivated by reaction with hydroxyl protecting groups of which a large number are known in the art. Hydroperoxides or peroxides, introduced e.g. by the methods of U.S.20120029154, may be inactivated by treatment with reducing agents such as thiols or reducing metal ions, e.g. $Fe^{2+}$.

c) contacting the particles with a composition comprising a polymerizable monomer 103.

The particles may be immersed in a solution of one or more polymerizable monomers, which is allowed to diffuse into the particles and come into intimate contact with the grafting sites. The monomer(s) can suitably have a low molecular weight, e.g. below 200 Da or below 100 Da, which ensures an easy penetration into the core, even when the core starts to be blocked by grafted polymer chains in step d). Suitable monomers can be vinyl monomers (including e.g. vinyl amides, vinyl esters, vinyl ethers, vinyl aryls, acrylates, acrylamides, methacrylates, and methacrylamides). The monomer(s) may e.g comprise a vinyl amide monomer, such as a monomer selected from the group consisting of N-vinyl pyrrolidone, N-vinyl caprolactam, N-vinyl formamide and N-vinyl acetamide. It can e.g. comprise N-vinyl pyrrolidone. Other suitable monomers include vinyl ethers, e.g. hydroxyethyl vinyl ether, diethyleneglycol vinyl ether or methacrylates, such as hydroxyethyl methacrylate or glycerol monomethacrylate. It is further possible to use a mixture of monomers, e.g. including a crosslinking (bifunctional or multifunctional) monomer. A vinyl amide such as N-vinyl pyrrolidone may e.g. be combined with a bi- or multifunctional methacrylate such as glycerol dimethacrylate. Apart from vinyl monomers it is also possible to use other polymerizable monomers, e.g. epoxide monomers such as ethylene or propylene oxide or oxetanes.

d) initiating polymerization of the polymerizable monomer 104.

Polymerization can be initiated by adding an initiator, or having an initiator as a component of the monomer composition in step c) and triggering initiation, e.g. by increasing the temperature for a thermal initiator, adding a coinitiator for a dual initiator system, or irradiating a photoinitiator by UV or visible light. This also applies for the case if the grafting sites are immobilized initiator groups. Alternatively, polymerization may be initiated by irradiation with ionizing radiation, such as gamma radiation or an electron beam. After polymerization, any residual monomers and other reagents, as well as non-grafted polymer, may be washed out of the particles. If a crosslinking monomer is used, the level should be low in order to avoid a crosslinked reaction solution, preferably below 2% (calculated based on the total amount of monomers). The molecular weight and morphology of the formed polymer can be controlled by varying initiator concentration, monomer concentration, crosslinker concentration, by using chain transfer agents or different reaction solvents.

The method may also comprise a step e) of reacting the particles with a ligand precursor reagent to couple ligands to the shell region. Step e) may be performed either after step d) or after step b) and before steps c) and d). If the inactivation of grafting sites in b) involves a reaction that simultaneously produces groups suitable for reaction with ligand precursor reagents, step e) can advantageously be conducted after step b). This can e.g. be the case when unsaturated grafting sites are inactivated by aqueous halogen, forming halohydrins which are easily reacted with nucleophilic ligand precursor reagents such as amines and sulfite ions. With large ligands like e.g. proteinaceous affinity ligands, it can be advantageous to perform step e) after step d), as the grafted polymer prevents the large ligand molecules to enter the core and there is no risk of losing expensive ligand by coupling in the core. With the ligands coupled only in the shell, they are all available for binding and contributing to the binding capacity.

In some embodiments, the porous support material comprises carbon-bound hydroxyl groups and the method comprises:

in step a') reacting the particles with an allylation reagent to obtain at least 50 micromole/ml allyl groups covalently attached to the particles; and in step b) reacting the particles first with a halogen for a period of up to 30 minutes and then with an alkaline aqueous solution.

In a third aspect, the invention discloses a method of separating a target biomacromolecule, comprising the steps of:

a) providing a sample comprising the target biomacromolecule;

b) conveying the sample through a column packed with the separation matrix as disclosed above;

c) optionally conveying a wash liquid through the column; and d) conveying an eluent through the column and recovering the target biomacromolecule in an eluate.

In some embodiments, the flow velocity through the column in step b) and/or d) is at least 70 cm/h, such as at least 150, at least 200 or 70-500, such as 70-300 or 150-300 cm/h.

In a fourth aspect, the invention discloses the use of the separation method disclosed above for improving resolution between the target biomacromolecule and at least one contaminant. The resolution may e.g. be improved in comparison with homogeneous matrices at flow velocities above 70 cm/h, above 150 or above 200 cm/h. Resolution is here defined according the standard definition, where the resolution Rs of two peaks in a chromatogram is:

$$Rs = 2*[(t_R)_B - (t_R)_A]/[W_A + W_B]$$

where $(t_R)_A$ is the retention time of peak A, $(t_R)_B$ the retention time of peak B, $W_A$ the width of peak A and $W_B$ the width of peak B. The widths are here measured in time units. It is however equally possible to enter the retention volumes of peaks A and B and in that case using the peak widths measure in volume units. In liquid chromatography, resolution usually decreases at increasing flow velocities due to peak broadening, but the matrices of the invention are less susceptible to such loss.

EXAMPLES (ALL PERFORMED AT 22+/−2° C. UNLESS OTHERWISE STATED)

Example 1—Synthesis of 96 Micrometer Particle Prototypes

Allylation 300 g of drained crosslinked agarose beads of median diameter (d50v) 95.8 micrometers, Kav for dextran of Mw 50 kDa=0.5, washed with distilled water, were mixed with 300 ml 50% aqueous NaOH solution in a 2 liter flask. The flask was equipped with an overhead agitator and immersed in a 50° C. water bath. After 30 min under agitation, 93.2 ml allyl glycidyl ether (AGE) was added and the reaction allowed to proceed for another 18.5 h. The gel was washed with distilled water (one gel volume), ethanol (one gel volume) and finally distilled water (8 gel volumes). The allyl content (method below) was 0.288 mmol/ml.

Titration of Allyl Groups

The gel was washed with distilled water and a 1 ml sample of drained gel was taken out and suspended in 9 ml of water in a flask. Saturated bromine water was added until a yellow colour due to an excess of $Br_2$ persisted. The sample was evacuated under stirring to remove the bromine excess. The mixture was then transferred to a titration vessel and made up to 20 ml with distilled water. 2-3 drops of conc. nitric acid were added before titration of the free bromide ions with $AgNO_3$.

Bromination of Shell Region 600 g (mL) of the allylated agarose beads was transferred drained into a 4 L round bottomed flask together with 3 L of distilled water. Mechanical stirring was applied (250 rpm).

A solution of 3.375 mL bromine in 400 mL of water was prepared. The bromine solution (equivalent to the allyls in a 7 μm shell of the 95.8 μm bead) was added through a drop funnel during approximately 15 minutes at a stirring speed of 300 rpm. After 20 minutes the gel was washed with 10×1GV with distilled water.

Cation Exchanger Functionalization of Shell Region 619 g (mL) of shell brominated gel was transferred to a 2 L round bottom flask. 124 mL of distilled water and 148.5 g of sodium sulfite were added. Mechanical propeller stirring was applied and the solution was left for 30 min at 250 rpm. pH was adjusted to 12.5 by adding 50% NaOH and the flask was immersed into a water bath at 50° C. The reaction progressed for 21 h. The gel was washed 10×GV with distilled water. The content of sulfonate cation exchanger groups was found to be 0.073 mmol/ml by standard NaOH titration. The cation exchanger was used as intermediate for grafting.

Determination of Shell Thickness 6 g (mL) of shell brominated gel was transferred to a Falcon tube. 5.4 mL of distilled water and 624 μL of 50% aqueous NaOH were added. The tube was placed into a shaking table at 50° C. The reaction progressed for 18 h. The gel was washed 10×GV with distilled water. The amount of residual allyl groups was then determined by titration as described above and was found to be 0.288 mmol/ml. For calculation of the shell thickness, it was assumed that all allyls in the shell had been consumed by bromination/alkaline hydrolysis and that all allyls in the core remained. The ratio of the allyl content after bromination/alkali treatment ($a_a$) and the allyl content before these treatments ($a_b$) will then be equal to the core/core+shell volume ratio. Thus, the shell thickness d will be $d=R(1-(a_a/a_b)^{1/3})$, where R is the bead radius (47.9 micrometers). With $a_a$=0.214 mmol/ml and $a_b$=0.288, d will then be 4.5 micrometers.

Grafting of Vinylpyrrolidone in Allyl Core 25.4 g allylated gel slurry (intermediate) was transferred to a glass filter (por. 3). The gel was washed with 7×2 GV of distilled water followed by 3×1.5 GV of 1 M $Na_2SO_4$ and sucked dry. The dry gel was transferred to a 100 mL flask and 1 M $Na_2SO_4$ solution was added to a total weight of 36.6 g. 3.87 mL of vinyl pyrrolidone (VP), 36.3 μL of glycerol dimethacrylate (GDMA) and 0.081 g of α,α-azodiisobutyramidine dihydrochloride (ADBA) initiator was added. Nitrogen gas was bubbled through the reaction solution with a pasteur pipette for 20 min. The flask was immersed in a glycerol bath with the temperature set at 45° C. and the stirring rate at 250 rpm. After 17 hours, 32.5 g of distilled water was added and the suspension was allowed to stir for 30 min at the reaction temperature. The gel was transferred to a glass filter and was washed with 10 GV of distilled water. The reaction was let to stand in water in the refrigerator for 48 h and was then washed with 5×1 GV ethanol and finally 10×1 GV water again.

Further grafting experiments in 1 M $Na_2SO_4$ were performed in the same way with the amounts showed in Table 1. The experiments in water were performed in the same way except for the initial washing where the gel was washed with 10×GV of distilled water and distilled water was added to a total weight according to the table above.

TABLE 1

Grafting conditions for different prototypes

| Experiment | H$_2$O/1M Na$_2$SO$_4$ | g gel | % GDMA | μL GDMA | % VP + GDMA | mL VP | % initiator | g ADBA |
|---|---|---|---|---|---|---|---|---|
| 1A | 1M Na$_2$SO$_4$ | 15 | 1 | 36.3 | 10 | 3.870 | 2 | 0.081 |
| 1B | 1M Na$_2$SO$_4$ | 15 | 1 | 36.3 | 10 | 3.870 | 5 | 0.203 |
| 1C | H$_2$O | 15 | 1 | 72.6 | 20 | 7.739 | 2 | 0.163 |
| 1D | H$_2$O | 15 | 1 | 72.6 | 20 | 7.739 | 5 | 0.407 |
| 1E | H$_2$O | 15 | 0 | 0 | 22.5 | 8.795 | 5 | 0.457 |
| 1F | 1M Na$_2$SO$_4$ | 15 | 0 | 0 | 11 | 4.300 | 20 | 0.894 |

The reaction mixtures had different viscosities and were not equally easy to wash after the reaction. The experiments performed in water were more viscous and harder to wash initially compared to those performed in sodium sulfate. Prototypes A and B had two layers when they were washed with water, one light layer that floated at the water surface and one heavy layer that sedimented to the bottom.

Dry Weight (Solids Content) Determination

The dry weight of 1 ml matrix was recorded on an evaporation balance (moisture analyser) after the grafting reaction and the results are shown in Table 2. The amount of grafted vinyl pyrrolidone-glycerol dimethacrylate copolymer (PVP-GDMA) was calculated from the difference in dry weight between the grafted and washed prototypes and the porous support material before the grafting.

TABLE 2

Dry weight for grafted prototypes.

| Prototype | Dry weight [mg/mL] | Dry weight base support [mg/mL] | PVP-(GDMA) or PVP attached [mg/mL] |
|---|---|---|---|
| 1A | 184 | 107 | 77 |
| 1B | 204 | 107 | 97 |
| 1C | 188 | 107 | 81 |
| 1D | 204 | 107 | 97 |
| 1E | 204 | 107 | 97 |
| 1F | 233 | 107 | 126 |

Coupling of Dextran to Allyl Core 40 g drained intermediate was mixed with 45 ml water and glycidyl methacrylate (GMA) was added under agitation. The radical initiator 2,2'-azobis-(2-aminopropane) HCl was added under a nitrogen atmosphere and the nitrogen flow was continued for 15 min at room temperature, after which the temperature was raised to 55° C. and the reaction was continued for 2.5 h at 55° C. The gel was then filtered and washed with distilled water, acetone and distilled water. After storing the gel in a refrigerator over a weekend, 30 g drained gel was mixed with a solution of 30 g dextran (Mw 5000 in 1G and 1H and Mw 3500 in 1I) in 60 ml distilled water. 7.91 ml 50% aqueous NaOH was added and the reaction mixture was kept under agitation at 50° C. over night. The gel was then filtered and washed with water.

TABLE 3

Dextran coupled prototypes

| Prototype | GMA (g) | Initiator (mg) | Dry weight base support (mg/mL) | Dry weight with GMA (mg/mL) | GMA attached (mg/mL) | Dry weight with dextran (mg/mL) | Dextran attached (mg/mL) |
|---|---|---|---|---|---|---|---|
| 1G | 2.5 | 48 | 114 | 142 | 20 | 151 | 8.7 |
| 1H | 3.8 | 72 | 114 | 172 | 58 | 176 | 4.8 |
| 1I | 5.1 | 96 | 114 | 194 | 80 | 206 | 12.9 |

As seen from Table 3, the amounts of dextran attached were very low, indicating that the dextran molecules did not penetrate efficiently into the core.

Example 2—Synthesis of 40 Micrometer Particle Prototypes

Allylation 300 g of drained crosslinked agarose beads of median diameter (d50v) 40 micrometers, Kav for dextran of Mw 124 kDa=0.5, prepared according to the methods described in U.S. Pat. No. 6,602,990, which is hereby incorporated by reference in its entirety, were washed with distilled water and mixed with 300 ml 50% aqueous NaOH solution in a 2 l flask. The flask was equipped with an overhead agitator and immersed in a 50° C. water bath. After 30 min under agitation, 93.2 ml allyl glycidyl ether (AGE) was added and the reaction allowed to proceed for another 18.5 h. The gel was washed with distilled water (one gel volume), ethanol (one gel volume) and finally distilled water (8 gel volumes). The allyl content (method below) was 0.283 mmol/ml.

Bromination of Shell Region (Aiming at 5 Micrometer Shell Thickness)

245 g of the allylated gel slurry (containing 140 ml drained gel) was transferred to a glass filter and washed three times with water. After draining, the gel was transferred to a 2 L flask and water was added to give a total weight of 800 g. 227.9 g aqueous bromine (1.60% w/w) was added to the flask over a period of 30-60 s under vigorous stirring. The reaction was allowed to progress for another 15 min. The gel was then washed with water (5 gel volumes).

2A. Inactivation of Shell Region 30 ml of the brominated gel was slurried with 25 ml water and 5.07 ml 50% aqueous NaOH (1.6 M) in a 250 ml flask. Under stirring, the flask was immersed in a 50° C. water bath for 18 h. The gel was then washed with water (10 gel volumes). The remaining allyl content was determined on a sample of this gel (for a 5 micrometer shell, the theoretical allyl level should be 0.121 mmol/ml). The allyl content was 0.182 mmol/ml, which corresponds to a shell thickness of 3 micrometers, calculated as described above.

2B. Cation Exchanger Functionalization of Shell Region 54 ml of the brominated gel was slurried with 16.5 g sodium sulfite in 55 ml water in a 250 ml flask. The pH was adjusted to 11.9 by addition of 50% aqueous NaOH. Under stirring, the flask was immersed in a 50° C. water bath for 18 h. After neutralization with 60% acetic acid, the gel was then washed with water (10 gel volumes). The content of sulfonate cation exchanger groups was found to be 0.065 mmol/ml by standard NaOH titration.

2C. Anion Exchanger Functionalization of Shell Region 54 ml of the brominated gel was slurried with 20 ml water and 9.8 ml trimethylammonium chloride (TMAC) in a 250 ml flask. The pH was adjusted to 11.5 by addition of 50% aqueous NaOH. Under stirring, the flask was left at room temperature (22° C.) for 18 h. After neutralization with 60% acetic acid, the gel was then washed with water (10 gel volumes). The content of quaternary ammonium anion exchange groups was found to be 0.101 mm/ml by standard chloride ion capacity titration.

2D. Inactivation of Core Region (Cation Exchanger Shell)

25 ml of the gel from B. was slurried with 25 ml water and 1.0 g NaOAc*3H$_2$O in a flask. After shaking, bromine water was added until a persistent yellow colour was obtained. Sodium formiate was then added to quench the excess of bromine. The gel was washed with 10 volumes of water and was after draining mixed with 20.8 ml water and 4.225 ml 50% aqueous NaOH (1.6 M) in a 100 ml flask. Under stirring, the flask was immersed in a 50° C. water bath for 19 h. The gel was then washed with water (10 gel volumes) and stored in 20% aqueous ethanol containing 0.2 M acetate.

2E. Inactivation of Core Region (Anion Exchanger Shell)

25 ml of the gel from C. was slurried with 25 ml water and 1.0 g NaOAc*3H$_2$O in a flask. After shaking, bromine water was added until a persistent yellow colour was obtained. Less Br$_2$(aq) was needed when brominating the allyl core than for D. Sodium formiate was then added to quench the excess of bromine. The gel was washed with 10 volumes of water and was after draining mixed with 20.8 ml water and 4.225 ml 50% aqueous NaOH (1.6 M) in a 100 ml flask. Under stirring, the flask was immersed in a 50° C. water bath for 19 h. The gel was then washed with water (10 gel volumes) and stored in 20% aqueous ethanol.

2F. Grafting of Vinylpyrrolidone in Allyl Core, Inactivated Shell 10 g drained gel from A. was mixed with 65 g water in a 250 ml flask. 0.5 g 2,2'-azobis(2-methylpropionamidine) dihydrochloride (AAPH) initiator and 24.5 g vinylpyrrolidone (VP) were added to the flask. After bubbling with N$_2$ for 4 minutes, the flask was immersed in a 55° C. water bath for 18 h. The highly viscous slurry was then washed on a glass filter with water (5 gel volumes), ethanol (>10 gel volumes) and 10 times with water (5 gel volumes each) and the gel was stored in 20% aqueous ethanol.

2G. Grafting of Vinylpyrrolidone in Allyl Core, Cation Exchanger Shell

Same procedure as in F, but using the gel from B. The product was stored in 20% aqueous ethanol containing 0.2 M acetate.

2H. Grafting of Vinylpyrrolidone in Allyl Core, Anion Exchanger Shell

Same procedure as in F, but using the gel from C. The product was stored in 20% aqueous ethanol.

2I. Coupling of Allyl Dextran to Allyl Core and Grafting of Vinylpyrrolidone to Allyl Dextran 15 ml of gel 2A, 15 ml o water and 0.6 g NaOAc*3H$_2$O was mixed in a 100 ml flask. Bromine water was added until a persistent yellow colour was obtained. Excess bromine was quenched by adding sodium formiate. The gel was then washed with five volumes of water.

The brominated gel was added to a solution of 15 g allyl dextran (Mw 70 000, allyl content 1.4 mmol/g) in 15 ml water and the temperature was raised to 50° C. An extra 5 ml was added. After 90 minutes, 2.0 ml 50% aqueous NaOH and 80 mg sodium borohydride were added and the reaction was allowed to progress for 16.5 h under agitation. The gel was then washed 10 times with water.

13 g of the drained gel was mixed with 84.5 g water and 0.65 g AAPH initiator and 31.9 g vinylpyrrolidone were added. After 5 min nitrogen bubbling, the mixture was heated to 55° C. and allowed to react for 18.5 h. The viscous mixture was then washed on a glass filter five times with water, five times with ethanol and 10 times with water.

2J. Coupling of Allyl Dextran to Allyl Core and Grafting of Vinylpyrrolidone to Allyl Dextran, Cation Exchanger Shell Same procedure as in 2I, but starting with gel 2B.

2K. Coupling of Allyl Dextran to Allyl Core and Grafting of Vinylpyrrolidone to Allyl Dextran, Anion Exchanger Shell Same procedure as in 2I, but starting with gel 2C.

TABLE 4

Dry weight for allyl dextran prototypes

| Prototype | Dry weight of start allyl core gel (mg/ml) | Dry weight after allyl dextran coupling (mg/ml) | Allyl dextran attached (mg/ml) | Dry weight after PVP grafting (mg/ml) | PVP attached (mg/ml) |
|---|---|---|---|---|---|
| 2I | 140 | 184 | 44 | 322 | 138 |
| 2J | 158 | 184 | 26 | 300 | 142 |
| 2K | 170 | 192 | 22 | N/A | |

Example 3—Evaluation of the Protein Accessibilities of the Core and Shell Regions by Confocal Microscopy The accessibilities were evaluated by confocal fluorescence microscopy using fluorescently labeled protein probes, which allows a three-dimensional high resolution imaging of how the probes penetrate into the different regions.

Probes

A monoclonal IgG antibody, labeled with Alexa 488 fluorescent dye (Molecular Probes) Bovine serum albumin (BSA), labeled with Cy5 fluorescent dye (GE Healthcare) Cytochrome C, labeled with Cy5 fluorescent dye (GE Healthcare)

Prototypes 1E (from Example 1). 96 micrometer agarose beads with sulfonate cation exchange ligands (total ligand content 0.073 mmol/ml matrix) in a shell region and grafted polyvinylpyrrolidone (PVP) in the core region.

Reference—SP Sepharose 6FF, (GE Healthcare), 90 micrometer crosslinked agarose beads with sulfonate cation exchange ligands (0.194 mmol/ml matrix) homogeneously distributed throughout the beads.

Method

The beads were incubated in the probe solutions (300 mg protein/ml gel) for 4 h in Eppendorf tubes. They were then either washed or observed directly in the confocal microscope (SP8, Leica) equipped with a 63×1.20 water immersion objective.

The Cy 5 labelled proteins (BSA and Cytochrome C) were scanned in xy-direction and with section series (100 optical sections in z-direction (step size ~3.5 μm). Scan speed 400; Pixel size: 512×512; Frame average 2. Excitation wavelength 633 nm. Emitted fluorescent light detected between 650-800 nm.

For Mab-Alexa 488 Excitation wavelength 488 nm. Emitted fluorescent light detected between 490-555 nm. Other settings the same as above, For Mab-Alexa 488 and BSA-Cy5 the particles were scanned directly after incubation without any wash. As the Cytochrome C solution gave a higher background, the particles were washed with buffer by repeated dilution, centrifugation and decantation.

Results

Figure 7:
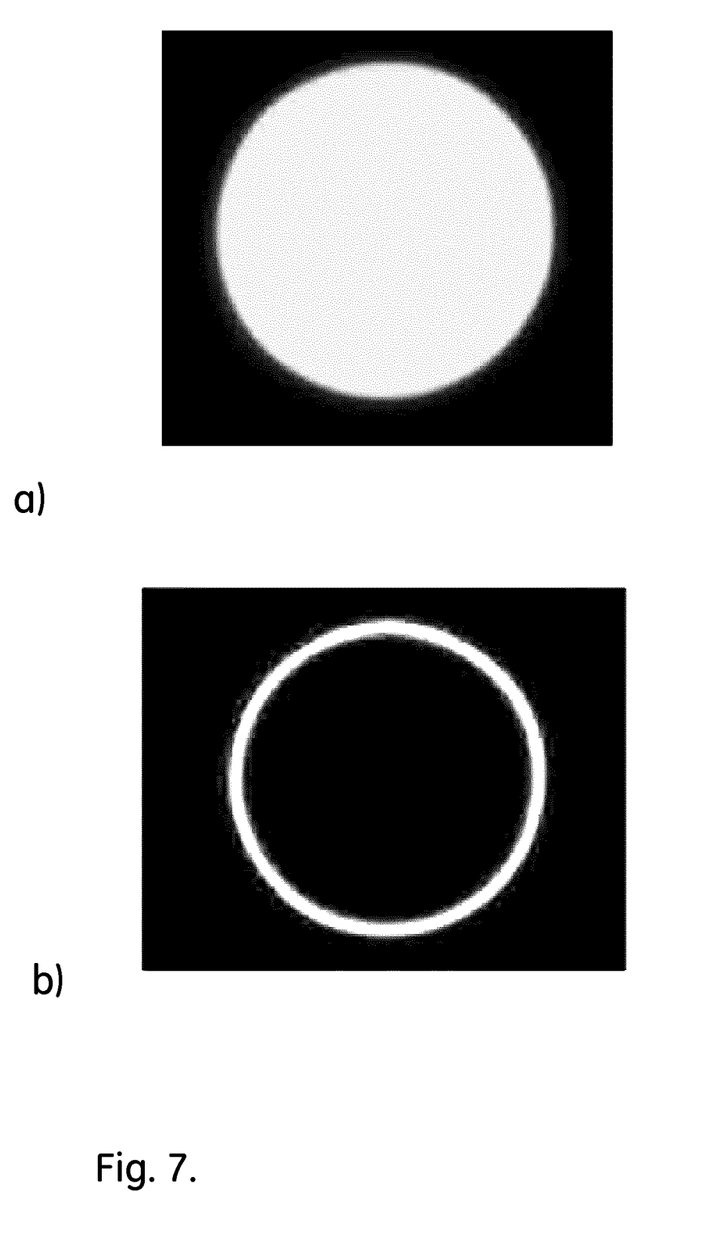
FIG. 7 shows confocal microscopy bead cross sections of a) SP Sepharose 6 FastFlow and b) prototype 1E, after incubation with a fluorescent monoclonal IgG antibody.
Figure 8:
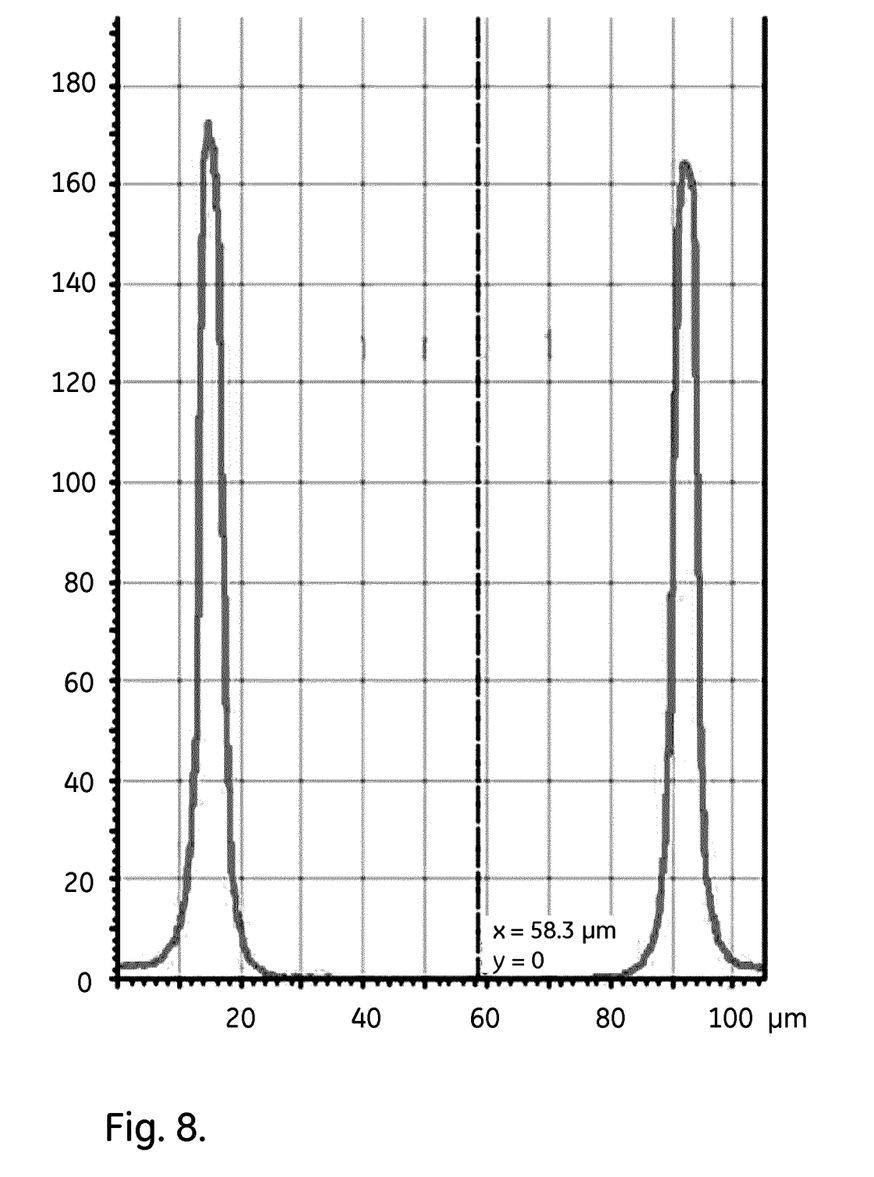
FIG. 8 shows the cross sectional intensity profile from the confocal microscopy cross section of FIG. 7 b).

As shown in FIG. 7 a), the reference beads adsorbed the proteins homogeneously throughout the beads. However, the prototype beads with ligands only in the shell region and a PVP-grafted core only adsorbed protein in the outermost 7-8 micrometers of the beads, corresponding to the shell region (FIGS. 7 b and 8). The small protein Cytochrome C (12 kDa) could penetrate the PVP-grafted core to some extent but did not remain there after washing, showing that it was only bound in the shell region. The results also show that the thickness of the shell region can be accurately determined from an intensity profile obtained in the confocal microscope (FIG. 8).

Figure 3:
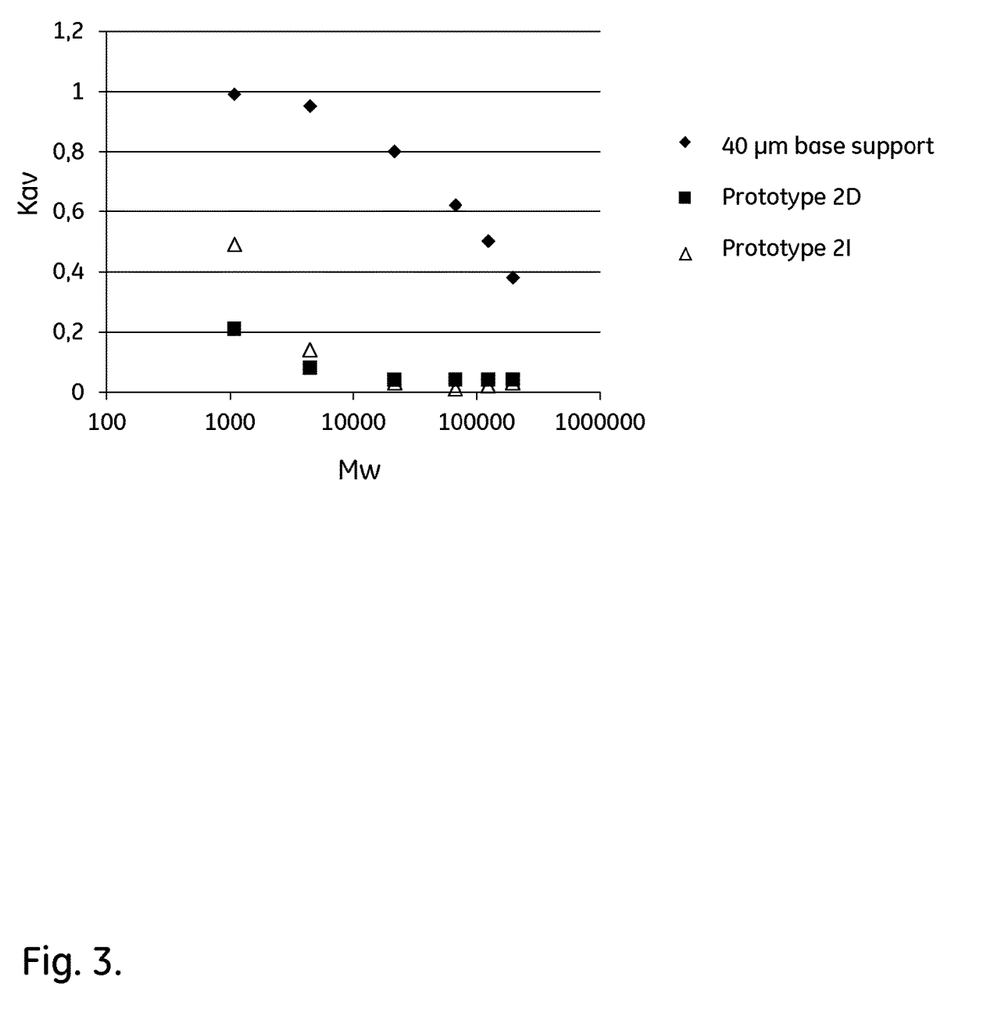
FIG. 3 shows size exclusion chromatography data for dextrans of different molecular weight, expressed as Kav, for columns packed with prototypes 2D and 2I and the 40 micrometer base support crosslinked agarose beads.

Example 4—Evaluation of the Protein Accessibilities of the Core and Shell Regions by Size Exclusion Chromatography Prototypes 2D and 2I, along with non-modified 40 micrometer agarose base particles were evaluated by size exclusion chromatography. The beads were packed in chromatography columns and solutions of dextrans of different molecular weights were applied to the columns and eluted. The $K_{av}$ values (the fraction of the pore volume accessible to probe molecules of a particular molecular weight) for the different dextrans were calculated from the retention times according to standard methods, as described in Gel Filtration Principles and Methods 5$^{th}$ edition, Pharmacia LKB 1991 (ISBN 91-97-0490-2-6), pp 8-11. The Kav vs. log Mw curves obtained are shown in FIG. 3 and Table 5, and demonstrate that the average accessibility of the dextrans has been dramatically decreased by the core grafting.

TABLE 5

Inverse size exclusion chromatography using dextran probes.

| Dextran, Mw | Support material $K_{AV}$ | Prototype 2D $K_{AV}$ | Prototype 2I $K_{AV}$ |
|---|---|---|---|
| 196000 | 0.38 | 0.04 | 0.03 |
| 123600 | 0.50 | 0.04 | 0.02 |
| 66700 | 0.62 | 0.04 | 0.01 |
| 21400 | 0.80 | 0.04 | 0.03 |
| 4440 | 0.95 | 0.08 | 0.14 |
| 1080 | 0.99 | 0.21 | 0.49 |

Example 5—Chromatographic Evaluation of 96 Micrometer Prototypes

The cation exchanger prototypes were packed in columns and different standard protein mixtures were injected and eluted at different flow rates. The peak widths and resolutions between particular protein pairs were determined. Dynamic binding capacities were determined with beta-lactoglobulin.

Test Protein Mixtures

Mix 1—An IgG monoclonal antibody and cytochrome C
Mix 2—Conalbumin, polyclonal IgG, cytochrome C and lysozyme
Mix 3—An IgG monoclonal antibody, cytochrome C and lysozyme Prototypes

TABLE 6

90-96 micrometer prototypes evaluated

| Prototype | | Grafted/coupled polymer (mg/ml) |
|---|---|---|
| 1A | PVP/GDMA core | 77 |
| 1B | PVP/GDMA core | 97 |
| 1C | PVP/GDMA core | 81 |
| 1D | PVP/GDMA core | 97 |
| 1E | PVP core | 97 |

TABLE 6-continued 90-96 micrometer prototypes evaluated

| Prototype | | Grafted/coupled polymer (mg/ml) |
|---|---|---|
| 1F | PVP core | 126 |
| Ref (SP FF) | Homogeneous | — |

Methods

The prototypes were packed in Tricorn 10/150 columns (GE Healthcare) with 10 mm inner diameter to bed heights of 8 mm, at a final packing flow rate of 3.0 ml/min.

The columns were equilibrated with 3 volumes of 50 mM Na-acetate pH 5.0 (A-buffer) at 2 ml/min before injection of 200 microliters of sample at 1 ml/min. Washing was done with 2 volumes of A-buffer at 2 ml/min, before elution with a 15 column volume gradient of 100% A-buffer to 100% B-buffer (25 mM Na-phosphate, pH 7.0+0.4 M NaCl) at 1 ml/min (1-3 ml/min in flow rate variation tests). The columns were further eluted with 2 volumes B-buffer at 1/1-3 ml/min (i.e. flow velocity 76 and 76-230 cm/h) and re-equilibrated with A-buffer at 2 ml/min.

For dynamic capacity determination, the columns were equilibrated with 100 mM citrate pH 3.0 and 3.8 mg/ml beta-lactoglobulin in 100 mM citrate pH 3.0 was loaded at 2 ml/min until the effluent absorbance ($A_{280}$) reached 20% of the feed absorbance ($A_{280}$). The columns were then cleaned with two volumes 1 M NaOH at 1 ml/min and reequilibrated with 100 mM citrate pH 3.0.

The columns were also tested in non-binding mode with cytochrome C in 50 mM Na-phosphate pH 6.8+0.4 M NaCl at 1 ml/min flow rate. The column volume (Vc), the cytochrome C elution volume (Vt), the peak asymmetry (As), the plate number (N/m) and the plate height (h) were measured.

Results

TABLE 7

Cytochrome C, non-binding conditions

| Prototype | Bed height (cm) | Vc (ml) | Vt (ml) | As | N/m | H (cm) |
|---|---|---|---|---|---|---|
| 1A | 14.4 | 11.3 | 6 | 1.64 | 600 | 0.167 |
| 1B | 15 | 11.8 | 5.82 | 1.83 | 476 | 0.21 |
| 1C | 15.4 | 12.1 | 6.05 | 1.92 | 954 | 0.105 |
| 1D | 15.6 | 12.3 | 5.86 | 1.77 | 1501 | 0.067 |
| 1E | 15.3 | 12.0 | 5.7 | 1.78 | 1654 | 0.06 |
| 1F | 14.6 | 11.5 | 5.33 | 2.18 | 1343 | 0.074 |
| Ref (SP FF) | 14.3 | 11 | 12.23 | 1.22 | 966 | 0.105 |

The cytochrome C results in Table 7 show that the retention volume Vt for PVP/GDMA and PVP core materials is about half the Vt for the reference, showing that cytochrome C is only retarded in the shell of the beads.

TABLE 8

Evaluation with protein mix 1

| Prototype | Vt mAb (ml) | Peak width mAb (ml) | Vt cyt C (ml) | Peak width cyt C (ml) | Resolution |
|---|---|---|---|---|---|
| 1A | 77.5 | 4.09 | 107.5 | 3.15 | 4.9 |
| 1B | 80.0 | 4.2 | 112.7 | 3.98 | 4.7 |
| 1C | 74.5 | 3.2 | 110.8 | 2.51 | 7.5 |
| Ref(SP FF) | 93 | 6.8 | 126 | 4.99 | 3.35 |

Figure 4:
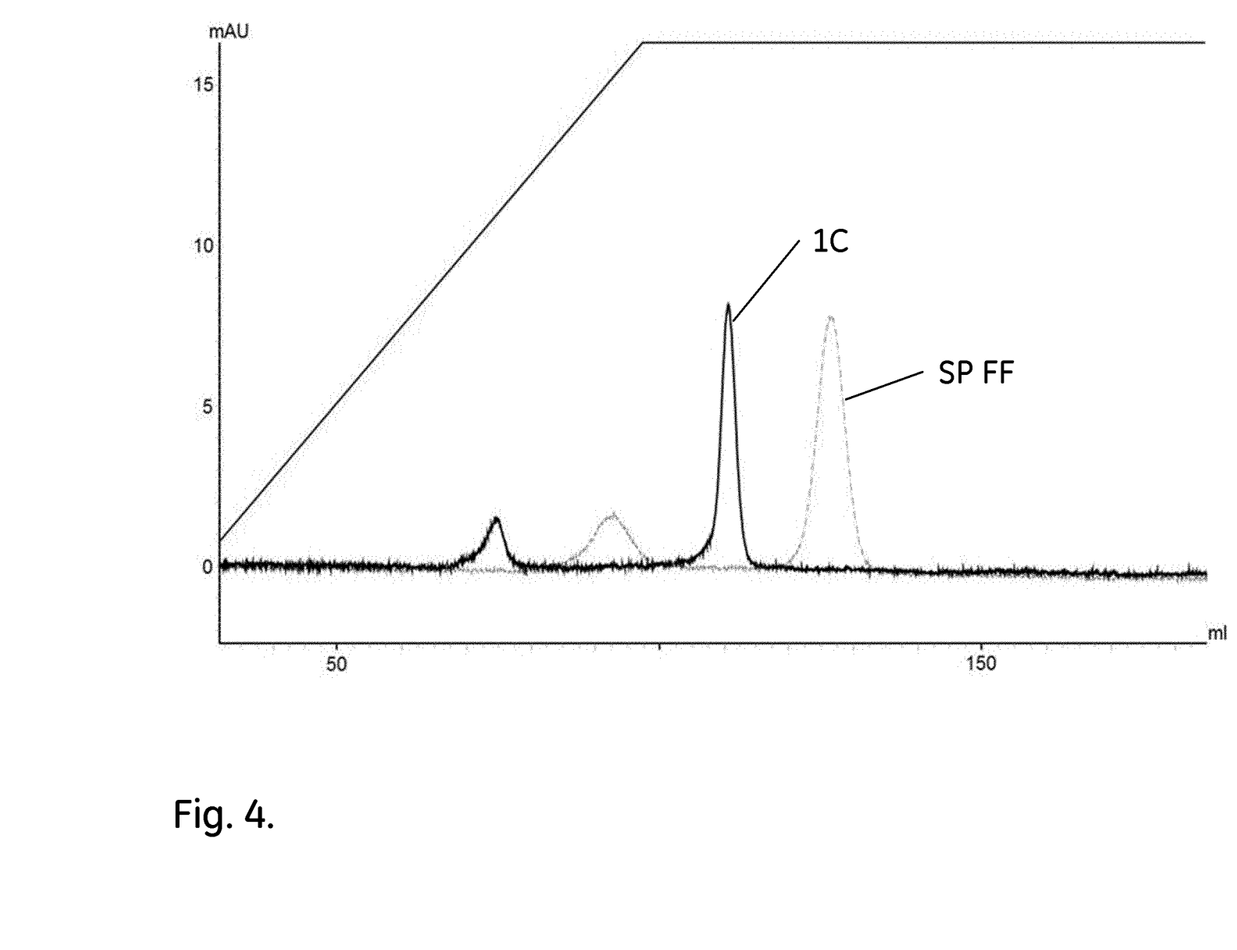
FIG. 4 shows chromatograms of mAb–cytochrome C mixtures on prototype 1C and the reference SP Sepharose 6 FastFlow (SP FF).

The results in Table 8 and FIG. 4 show that the prototypes give considerably narrower peaks and an increased resolution between mAb and cytochrome C in comparison with the reference.

TABLE 9

Evaluation with protein mix 2.

| Prototype | Resolution conalb/cyt C | Resolution cyt C/lys | Peak width cyt C (ml) | Peak width lys (ml) | Vt conalb (ml) | Vt cyt C (ml) | Vt lys (ml) |
|---|---|---|---|---|---|---|---|
| 1A | 2.29 | 2.6 | 3.8 | 4.4 | 78 | 118.9 | 136.8 |
| 1B | 2.28 | 2.32 | 5 | 5.2 | 79.3 | 122.7 | 142.8 |
| 1C | 2.91 | 3.84 | 3.2 | 4.2 | 77 | 122.5 | 146.6 |
| 1D | 2.86 | 3.85 | 3.25 | 4.2 | 78.6 | 124.4 | 148.9 |
| 1E | 3 | 4.08 | 3.03 | 3.67 | 76.5 | 121.4 | 144.6 |
| 1F | 2.73 | 3.8 | 2.84 | 3.34 | 75.2 | 117.5 | 137.5 |
| Ref (SP FF) | 1.6 | 1.6 | 5.8 | 6.6 | 90.7 | 137.7 | 154.5 |

Figure 5:
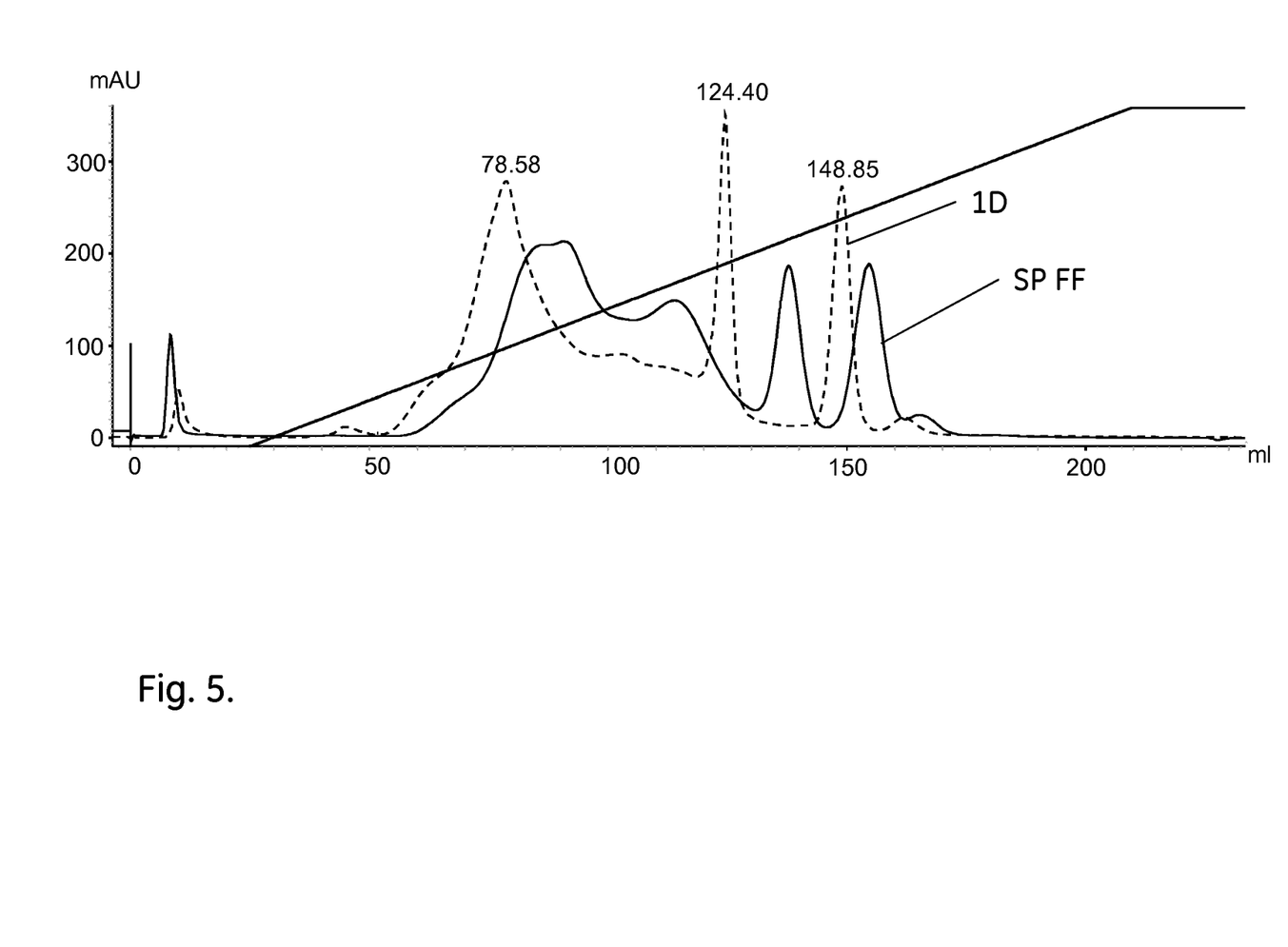
FIG. 5 shows chromatograms of conalbumin+polyclonal IgG+cytochrome C+lysozyme mixtures on prototype 1D and the reference SP Sepharose 6 FastFlow (SP FF).
Figure 6:
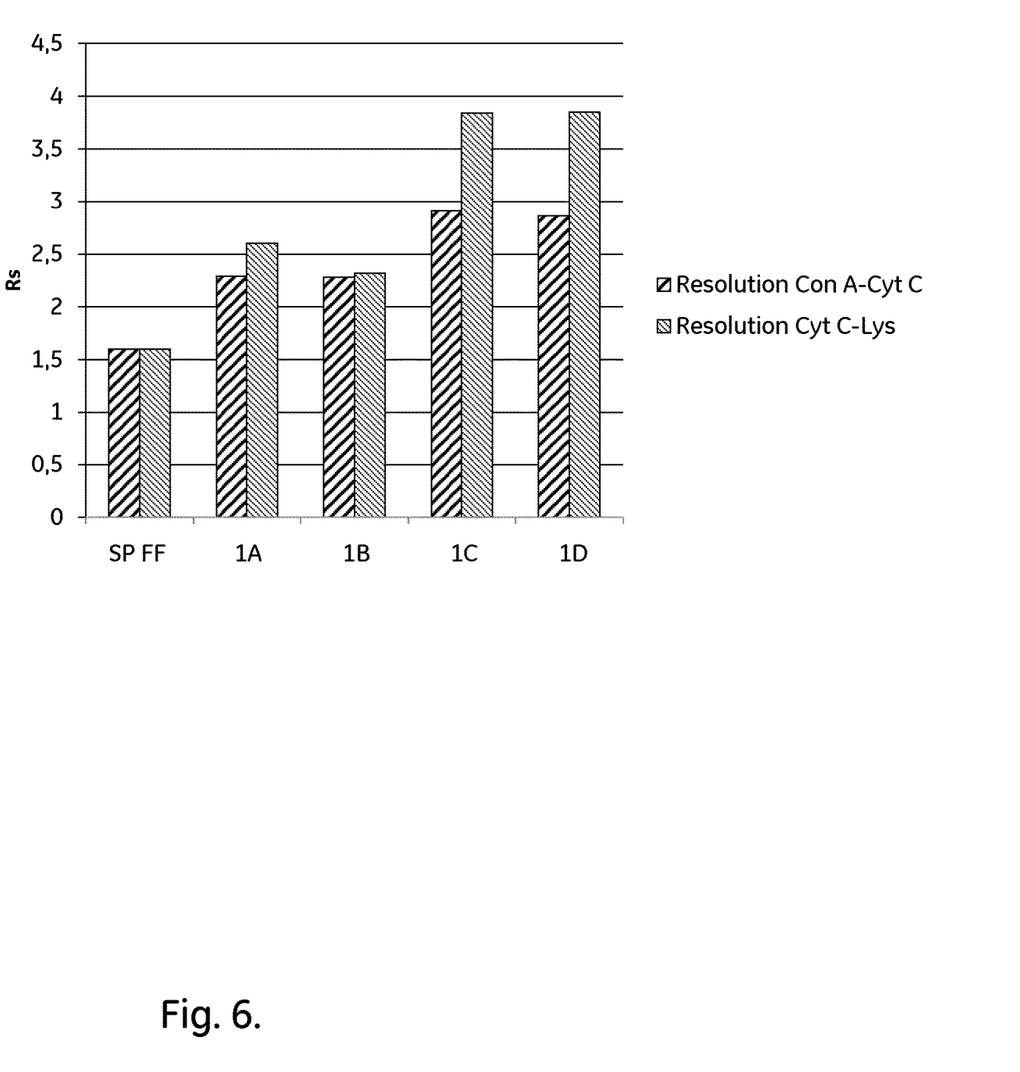
FIG. 6 shows resolution data for the protein pairs conalbumin+cytochrome C and cytochrome C+lysozyme on prototypes 1A-1D and the reference SP Sepharose 6 FastFlow (SP FF).

As shown in Table 9 and FIG. 5, all the PVP/GDMA and PVP prototypes showed considerably decreased peak widths and increased resolution in comparison with the reference.

TABLE 10

Peak widths for protein mix 3 at different flow rates.

| Prototype | Flow rate (ml/min) | Peak width mAb (ml) | Peak width cyt C (ml) | Peak width lys (ml) |
|---|---|---|---|---|
| 1D | 1 | 3.88 | 3.04 | 4.28 |
|  | 2 | 4.31 | 3.49 | 5.04 |
|  | 3 | 4.65 | 3.8 | 5.58 |
| 1E | 1 | 3.66 | 2.83 | 3.93 |
|  | 2 | 4.16 | 3.32 | 4.67 |

TABLE 10-continued

Peak widths for protein mix 3 at different flow rates.

| Prototype | Flow rate (ml/min) | Peak width mAb (ml) | Peak width cyt C (ml) | Peak width lys (ml) |
|---|---|---|---|---|
|  | 3 | 4.56 | 3.69 | 5.28 |
| 1F | 1 | 3.6 | 2.73 | 3.53 |
|  | 2 | 4.12 | 3.2 | 4.23 |
|  | 3 | 4.57 | 3.6 | 4.78 |
| Ref (SP FF) | 1 | 7.34 | 5.59 | 6.99 |
|  | 2 | 9.53 | 7.42 | 9.29 |
|  | 3 | 11.13 | 9.16 | 11.2 |

TABLE 11

Resolution values for protein mix 3 at different flow rates.

| Prototype | Flow rate (ml/min) | Resolution mAb/cyt C | Resolution cyt C/lys |
|---|---|---|---|
| 1D | 1 | 6.19 | 3.93 |
|  | 2 | 5.53 | 3.31 |
|  | 3 | 5.13 | 2.97 |
| 1E | 1 | 6.46 | 4.23 |
|  | 2 | 5.67 | 3.44 |
|  | 3 | 5.13 | 3.08 |
| 1F | 1 | 5.94 | 3.99 |
|  | 2 | 5.17 | 3.29 |
|  | 3 | 4.63 | 2.92 |
| Ref (SP FF) | 1 | 3.11 | 1.58 |
|  | 2 | 2.43 | 1.12 |
|  | 3 | 2.05 | 0.91 |

Tables 10 and 11 show that, again, the prototypes give narrower peaks and higher resolution than the reference. They also show that the prototypes are less sensitive to peak broadening and loss of resolution at higher flow rates in comparison with the reference.

TABLE 12

Dynamic capacities at 10% breakthrough
(Qb 10%) with beta-lactoglobulin.

| Prototype | Qb 10% (mg/ml) |
|---|---|
| 1D | 38.6 |
| 1E | 38.6 |
| 1F | 38.5 |
| Ref (SP FF) | 106.8 |

Although the prototypes still have a significant binding capacity, they have lost about ⅔ of the capacity in comparison with the reference. It is expected that this can be optimized by varying the shell thickness and the ligand content.

Example 6—Chromatographic Evaluation of 40 Micrometer Prototypes

Prototypes 2G and 2J and the reference material Capto SP ImpRes (SP cation exchanger based on 40 micrometer highly crosslinked agarose beads, with 0.13-0.16 mmol/l homogeneous ligand content) were packed in Tricorn 10/100 columns to bed heights of 6.5 cm and bed volumes of 5.0 ml. Pack flow 22-38 ml/min.

Peak widths were evaluated by single protein injections of cytochrome C (4 mg/ml, 200 μl) and lysozyme (4 mg/ml, 200 μl), with A buffer 50 mM Na-acetate pH 5.0 and B buffer 25 mM Na-phosphate pH 6.8+0.4 M Na Cl and a 15 column volume 0-100% B buffer linear gradient at 1.0 ml/min flow rate. The results are shown in Table 13 and indicate that also these prototypes decreased the peak width compared to the homogeneous reference.

TABLE 13

Peak widths 40 micrometer prototypes

| Prototype | Peak width cyt C (ml) | Peak width lys (ml) |
|---|---|---|
| 2G | 1.37 | 1.92 |
| 2J | 1.18 | 1.56 |
| Ref (SP ImpRes) | 2.26 | 2.27 |

Dynamic capacities (Qb 10%) were measured with beta-lactoglobulin at flow velocities 76-306 cm/h and the results are shown in Table 14. The loss of capacity was approx. 50% compared to the reference.

TABLE 14

Dynamic capacities 40 micrometer prototypes

| Prototype | Flow velocity (cm/h) | Qb 10% (mg/ml) |
|---|---|---|
| 2G | 76 | 31.6 |
|  | 153 | 31.7 |
|  | 306 | 31.0 |
| Ref (SP ImpRes) | 76 | 64.6 |
|  | 153 | 62.2 |
|  | 306 | 64.9 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

The invention claimed is:

1. A separation matrix for purification of biomacromolecules, comprising a plurality of particles having a core region and a shell region, wherein:
  a) said shell region is accessible to a target biomacromolecule, wherein said shell region does not comprise polymers grafted to a porous support material and does not comprise polymers grafted to said shell;
  b) said core region is less accessible to said target biomacromolecule than said shell region; and
  c) said core region comprises at least 50 mg/ml of a vinyl polymer grafted to the porous support material and comprising residues of at least one polymerizable monomer, wherein said vinyl polymer comprises vinyl amide monomer residues selected from the group consisting of N-vinyl pyrrolidone, N-vinyl caprolactam, N-vinyl formamide and N-vinyl acetamide.

2. The separation matrix of claim 1, wherein said core region is substantially inaccessible to said target biomacromolecule.

3. The separation matrix of claim 1, wherein a diffusion rate for said target biomacromolecule in the core region is less than 10% of the diffusion rate for said target biomacromolecule in the shell region.

4. The separation matrix of claim 1, wherein said target biomacromolecule is a protein with a molecular weight of over 5 kDa.

5. The separation matrix of claim 1, wherein said target biomacromolecule is an immunoglobulin.

6. The separation matrix of claim 1, wherein said shell region has an average thickness (d) of 1-15 micrometers.

7. The separation matrix of claim 1, wherein said shell region has an average thickness of 0.5 to 6% of the diameter or the sphere-equivalent diameter of said particles.

8. The separation matrix of claim 1, wherein said core region has a molecular weight cutoff for globular proteins of 1 to 500 kDa.

9. The separation matrix of claim 1, wherein said particles are substantially spherical.

10. The separation matrix of claim 1, wherein said particles have a volume-weighted median diameter of 10-400 micrometers.

11. The separation matrix of claim 1, wherein said shell region and said core region both comprise said porous support material.

12. The separation matrix of claim 11, wherein said porous support material comprises a polysaccharide.

13. The separation matrix of claim 12, wherein said polysaccharide comprises agarose or agar.

14. The separation matrix of claim 12, wherein said polysaccharide is crosslinked.

15. The separation matrix of claim 1, wherein said vinyl polymer is grafted to said support material via bonds or linkers.

16. The separation matrix of claim 1, wherein said vinyl polymer comprises N-vinyl pyrrolidone monomer residues.

17. The separation matrix of claim 1, wherein said shell region comprises ligands capable of binding said target biomacromolecule.

18. The separation matrix of claim 17, wherein said ligands comprise positively or negatively charged groups.

19. The separation matrix of claim 17, wherein said ligands comprise hydrophobic groups.

20. The separation matrix of claim 17, comprising multimodal ligands.

21. The separation matrix of claim 17, wherein said ligands comprise affinity groups.

22. The separation matrix of claim 17, wherein said shell region comprises 10-20 000 micromol/ml ligands.

23. The separation matrix of claim 4, wherein said protein has a molecular weight of over 20 kDa.

24. The separation matrix of claim 5, wherein said target biomacromolecule is IgG.

25. The separation matrix of claim 15, wherein said linkers have a structure selected from the group consisting of structures I, II, III, IV or V:

Sup-O-$CH_2$-$CH_2$-$CH_2$-Pol (I)
Sup-O-$CH_2$-CH($CH_3$)-Pol (II)
Sup-O-$CH_2$-CHOH-$CH_2$-O-$CH_2$-$CH_2$-$CH_2$-Pol (III)
Sup-O-$CH_2$-CHOH-$CH_2$-O-$CH_2$-CH($CH_3$)-Pol (IV)
Sup-O-Pol (V), wherein Sup denotes the support material and Pol the vinyl polymer.

26. The separation matrix of claim 20, wherein said multimodal ligands are selected from the group consisting of N-benzyl-N-methyl ethanolamine, N-benzoyl homocysteine, 4-mercaptoethyl pyridine, p-aminobenzamidoacetic acid, tryptophan and phenylalanine.

27. A method of manufacturing a separation matrix of claim 1, comprising the steps of:
 a) providing a plurality of particles comprising a porous support material with grafting sites;
 b) inactivating said grafting sites in a shell region;
 c) incubating said particles in a composition comprising a polymerizable monomer wherein said polymerizable monomer is a vinyl amide; and
 d) initiating polymerization of said polymerizable monomer.

28. The method of claim 27, further comprising, before step a), a step a') of introducing grafting sites on a porous support material.

29. The method of claim 27, further comprising a step f) of reacting said particles with a ligand precursor reagent to couple ligands to said shell region.

30. The method of claim 27, wherein said porous support material comprises carbon-bound hydroxyl groups and wherein said method comprises:
 in step b) reacting said particles with an allylation reagent to obtain at least 50 micromole/ml allyl groups covalently attached to the particles; and
 in step c) reacting said particles with a halogen for a period of up to 30 minutes and then with an alkaline aqueous solution.

31. The method of claim 27, wherein said vinyl amide is N-vinyl pyrrolidone.

32. A method of separating a target biomacromolecule, comprising the steps of:
 a) providing a sample comprising said target biomacromolecule;
 b) conveying said sample through a column packed with the separation matrix of claim 1;
 c) optionally conveying a wash liquid through said column; and
 d) conveying an eluent through said column and recovering said target biomacromolecule in an eluate.

33. The method of claim 32, wherein a flow velocity through the column in step b) and/or d) is at least 70 cm/h.

* * * * *